May 23, 1961 H. C. SWIM Plant Pat. 2,056
ROSE PLANT
Filed Aug. 15, 1960
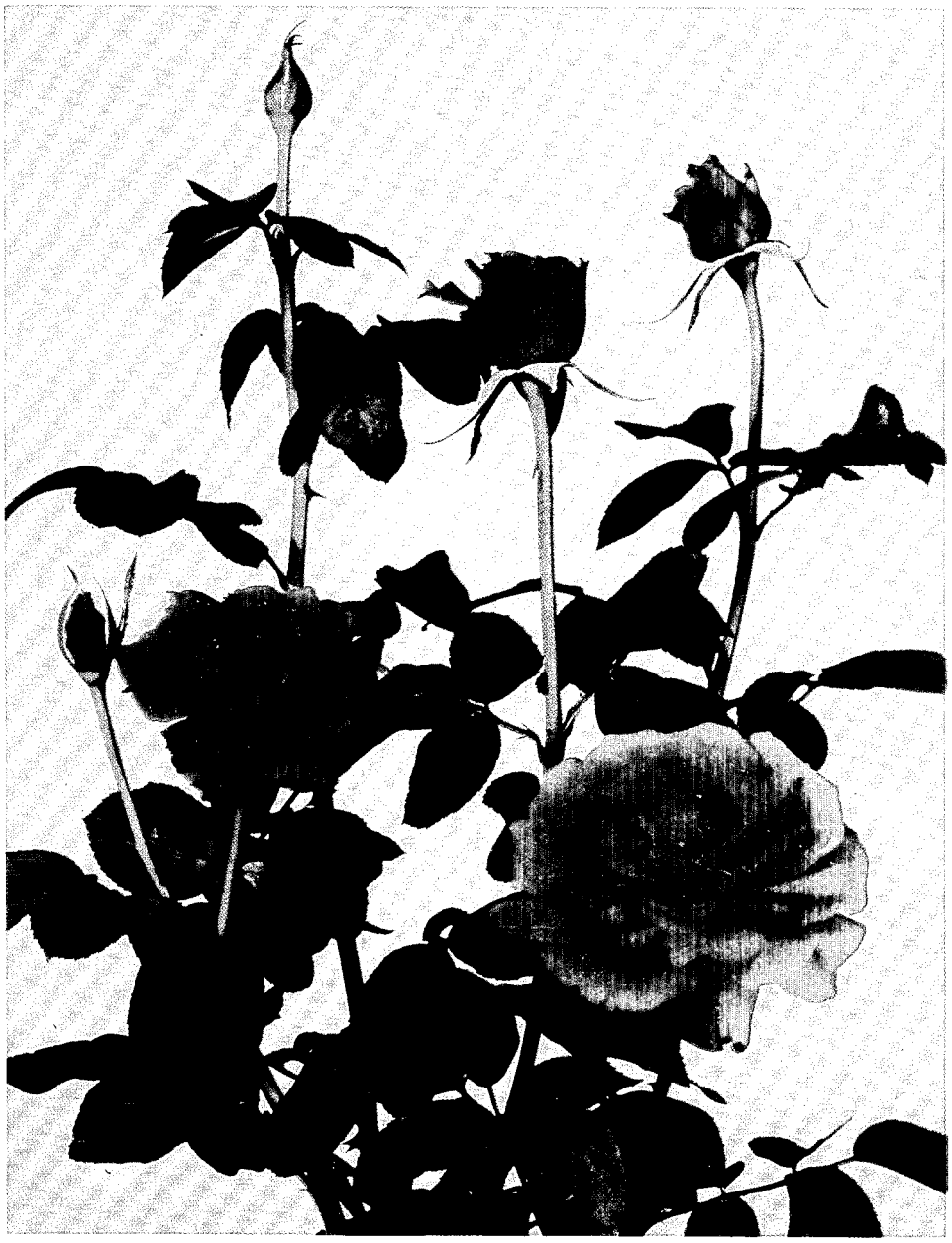
Inventor.
H. C. Swim
By: Robb & Robb
Attorneys.

United States Patent Office

Plant Pat. 2,056
Patented May 23, 1961

2,056

ROSE PLANT

Herbert C. Swim, Ontario, Calif., assignor to Armstrong Nurseries, Inc., San Bernardino, Calif., a corporation of California Filed Aug. 15, 1960, Ser. No. 49,807

1 Claim. (Cl. 47—61)

The present invention relates to a new and distinct variety of rose plant of a class intermediate the hybrid tea and floribunda classes, which was originated by me by crossing the variety "Charlotte Armstrong" (Pl. Pat. No. 455) and an unnamed and unpatented variety of the floribunda type, said latter parent variety being notable for its vigorous and upright habit of growth, a habit of bearing its flowers in clusters, with each flower being of a size averaging about 3 inches in diameter, being very double in petalage and of a light to medium scarlet orange color.

The general objective of this breeding was to produce a new rose variety having a plant habit at least as vigorous as that of its parent variety "Charlotte Armstrong," glossy, disease-resistant foliage comparable to that of the unnamed parent variety, a floriferousness greater than that of the variety "Charlotte Armstrong" and approaching that of the other parent variety, a habit of bearing flowers on stems of at least a medium length, with the flowers supported in an upright manner, said flowers also being at least moderately double in petalage and having a form approaching that of "Charlotte Armstrong" as nearly as possible, good flower substance comparable to that of the unnamed parent variety, and a pleasing flower color near red or orange-scarlet. This objective was substantially achieved, along with other desirable improvements, as evidenced by the following unique combination of characteristics which are outstanding in the new variety and which distinguish it from its parents, as well as from all other varieties of which I am aware:

(1) A vigorous, upright-spreading, well-shaped, sturdily-branched plant habit;

(2) Attractive, medium-sized, disease-resistant foliage, with mature foliage being of a dark green color and providing a pleasing contrast with the reddish color of the new foliage;

(3) A floriferousness somewhat greater than that of the parent variety "Charlotte Armstrong";

(4) A habit of bearing the flowers on strong stems of from short to medium length, with the flowers borne sometimes singly and sometimes in small clusters;

(5) A rather short bud form ranging from ovoid to urn-shaped in shape, said buds opening into well-formed, high-centered, very double flowers;

(6) A flower size ranging medium to large, though not as large as the flowers of "Charlotte Armstrong";

(7) A better-than-average petal substance, with attendant very long-lasting flower qualities and prolonged retention of flower form until the petals drop; and (8) A distinctive, bright, medium to dark red general color tonality of the flowers ranging between Currant Red and Cardinal Red, with prolonged retention of the flower color and consequent relative lack of fading or much blueing, considering the long life of the flowers.

In comparison with its seed parent "Charlotte Armstrong," the growth habit of the plant of the new variety is more stocky and somewhat more upright; the flower size is somewhat smaller; the flower petalge is considerably greater; the petal substance is also much greater, thus making the flower much longer lasting than the flowers of this parent variety; and the flower color is darker, ranging from medium to dark red, as compared with the much lighter red or dark pink color of the flowers of "Charlotte Armstrong."

As compared with the unnamed pollen parent, the new variety bears its flowers both singly and in small clusters, whereas this parent usually bears its flowers in fairly large clusters only; the flowers are substantially larger in size than those of this parent; and the flower color of the new variety is from medium to dark red, as distinguished from a more medium to light orange-scarlet in the case of the flowers of this parent.

Asexual reproduction of my new variety by budding, as performed at Ontario, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart and with Robert Ridgway's Color Standards and Nomenclature, as indicated:

Type: Bush; outdoor; seedling; for cut flowers and for garden decoration.

Class: Between hybrid tea and floribunda.

Breeding: Seedling.

*Seed parent.*—"Charlotte Armstrong."

*Pollen parent.*—An unnamed seedling of the floribunda type.

Propagation: Holds its distinguishing characteristic through succeeding propagations by budding.

*Flower*

Locality where grown and observed: Ontario, California.

Flowers borne: Sometimes singly, but usually from 2 to 5 or more per stem; in irregular clusters; on strong stems ranging from short to medium length.

Quantity of bloom: Free, outdoors.

Continuity: Nearly continuous during growing season.

Fragrance: Slight.

Bud:

*Peduncle.*—Average length; from average caliper to heavy; erect; usually smooth; with from several to many stipitate glands. Color—near Biscay Green, Plate XVII (Ridgway).

*Before calyx breaks.*—Size—from small to medium. Form—from short to medium length; pointed; ovoid.

*As calyx breaks.*—Color—near Purple Madder, Plate 1028, page 181 (Wilson), but near Maroon, Plate 1030, page 185 (Wilson) on areas exposed longer to sun.

*Sepals.*—Inner surface—with fine, woolly tomentum. Outer surface—usually with few small stipitate glands. Alternate margins—lined with fine, woolly tomentum. Other margins—lined with stipitate glands and occasional small, slender foliaceous appendages. Apex—often extended as foliaceous part beyond tip of bud up to ¼ to ½ its length.

*As first petal opens.*—Size—from small to average. Form—short; ovoid; often urn-shaped. Color: outside—between Cardinal Red, Plate 822, page 168 (Wilson) and Chrysanthemum Crimson, Plate 824, page 169 (Wilson), with small area at base near attachment near Canary Yellow, Plate 2/2, page 2 (Wilson); inside—near Cardinal Red, Plate 822/1, page 168 (Wilson), with areas exposed longer to sun near Chrysanthemum Crimson, Plate 824, page 169 (Wilson), and with small areas at base near attachment near Canary Yellow, Plate 2/2, page 2 (Wilson).

*Opening.*—Opens up well; is not retarded or prevented from opening by cold, hot, wet, or dry weather.

Bloom:

*Size (when fully open).*—Average; from 3½ to 4 inches.

*Petalage.*—Double; from 36 to 44 petals, plus from 2 to 6 petaloids; arranged irregularly.

*Form.*—High-centered at first, but becoming cupped to high-centered; petals at first being tightly cupped, with outer petals of open flower usually rolled outward both at apex and along edges; intermediate and inner petals of open flower usually nearly flat from base half way to apex, with remainder of petals usually having a more or less wavy surface, particularly toward the outer petal margins.

Petals:

*Texture.*—Medium thickness; moderately leathery. Inside—velvety. Outside—satiny.

*Shape.*—Outside—broadly obovate; usually with from 1 to 3 notches. Intermediate — obovate, with apex rounded to flat; usually with from 1 to 3 notches. Inside—narrowly obovate, with apex rounded; sometimes with one or two notches.

This description of a newly opened flower was made from a rose grown outdoors in the month of September, at Ontario, California:

*Color.*—Outer petal: outside surface—between Currant Red, Plate 821/3, page 167 (Wilson) and Cardinal Red, Plate 822/3, page 168 (Wilson), with small area at base near attachment near Canary Yellow, Plate 2/2, page 2 (Wilson) varying with weather conditions, with occasional blackening at outer margins, particularly at apex; inside surface —between Currant Red, Plate 821/2, page 167 (Wilson) and Cardinal Red, Plate 822/1, page 168 (Wilson), with small areas at base near attachment near Canary Yellow, Plate 2/2, page 2 (Wilson); varying with weather conditions, with occasional blackening at outer margins, particularly at apex. Intermediate petal: outside surface—between Currant Red, Plate 821/3, page 167 (Wilson) and Cardinal Red, Plate 822/3, page 168 (Wilson), with small area at base near attachment near Canary Yellow, Plate 2/2, page 2 (Wilson); varying with weather conditions, with occasional blackening at outer margins, particularly at apex; inside surface—between Currant Red, Plate 821/1, page 167 (Wilson) and Cardinal Red, Plate 822/1, page 168 (Wilson), with small area at base near attachment near Canary Yellow, Plate 2/2, page 2 (Wilson); varying with weather conditions, with occasional blackening at outer margins, particularly at apex. Inner petal: outside surface—between Currant Red, Plate 821/1, page 167 (Wilson) and Cardinal Red, Plate 822/1, page 168 (Wilson), with small area at base near attachment near Canary Yellow, Plate 2/2, page 2 (Wilson); inside surface—between Currant Red, Plate 821, page 167 (Wilson) and Cardinal Red, Plate 822, page 168 (Wilson), with small area at base near attachment near Canary Yellow, Plate 2/2, page 2 (Wilson).

This description was made from a rose that was open for three days outdoors in the month of September, at Ontario, California:

*Color.*—Outer petal: outside surface—between Cardinal Red, Plate 822/3, page 168 (Wilson) and Cardinal Red, Plate 822/2, page 168 (Wilson), with small area at base near attachment near Aureolin, Plate 3/2, page 3 (Wilson); varying with weather conditions, with occasional blackening at outer margins, particularly at apex; inside surface—near Cardinal Red, Plate 822/1, page 168 (Wilson), with small area at base near attachment near Aureolin, Plate 3/2, page 3 (Wilson); varying with weather conditions, with occasional blackening at outer margins, particularly at apex. Inner petal: outside surface—between Cardinal Red, Plate 822/3, page 168 (Wilson) and Cardinal Red, Plate 822/2, page 168 (Wilson), with small area at base near attachment near Aureolin, Plate 3/2, page 3 (Wilson); inside surface—between Currant Red, Plate 821/1, page 167 (Wilson) and Cardinal Red, Plate 822/1, page 168 (Wilson), with small area at base near Aureolin, Plate 3/2, page 3 (Wilson).

*General color effect.*—Newly opened flower—between Currant Red, Plate 821/1, page 167 (Wilson) and Cardinal Red, Plate 822/1, page 168 Wilson); varying with weather conditions, with occasional black spots being evident at petal margins. 3-days open—between Currant Red, Plate 821/1, page 167 (Wilson) and Cardinal Red, Plate 822/2, page 168 (Wilson); varying with weather conditions, with occasional black spots being evident at petal margins.

*Behavior.*—Drop off cleanly; not particularly affected by cold, hot, wet or dry weather.

*Flower longevity.*—On bush in garden—4 or 5 days in September. Cut roses grown outdoors and kept at living-room temperatures—6 or 7 days in September.

*Reproductive organs*

Stamens: Average number; arranged regularly about pistils.

Filaments: From short to medium length; from 4 to 10 mm. in length; most with anthers. Color—upper half of filament near Magenta, Plate 27/3, page 27 (Wilson), with remainder near Empire Yellow, Plate 603/2, page 66 (Wilson).

Anthers: Small; all open approximately at once. Color: upper side—margins near Maize Yellow, Plate 607, page 69 (Wilson), with remainder near Azalea Pink, Plate 618/3, page 74 (Wilson); under side—margins near Maize Yellow, Plate 607, page 69 (Wilson), with remainder near Azalea Pink, Plate 618/3, page 74 (Wilson).

Pollen: Moderately abundant. Color—near Cadmium Orange, Plate 8, page 8 (Wilson).

Pistils: Average number; approximately 75 in number.

Styles: Moderately even; from short to average length (from 3 to 8 mm.); from thin to average caliper; bunched. Color—upper third of style near Geranium Lake, Plate 20/1, page 20 (Wilson), with remainder near Canary Yellow, Plate 2/3, page 2 (Wilson).

Stigma: Color—near Straw Yellow, Plate 604/1, page 67 (Wilson).

Ovaries: Usually all enclosed in calyx.

Hips: Average length; between obovoid and globular in shape; smooth; walls thick and fleshy. Color (½ mature)—between Kildare Green, Plate XXXI (Ridgway) and Absinthe Green, Plate XXXI (Ridgway).

Sepals: Falling soon; medium length; curled; recurved. Color: inside—near Chrysolite Green, Plate XXXI (Ridgway); outside—near Courge Green, Plate XVII (Ridgway).

Seeds: From few to average number; from 18 to 25 in number; from small to medium size.

*Plant*

Foliage:

*Leaves.*—Compound of usually 3 to 7 leaflets; abundant; medium size; leathery; semi-glossy.

*Leaflets.*—Shape—between oval and oblong, with apex acute. Base—round. Margin—simple serrate.

*Color.*—Mature: upper surface—between Cedar Green, Plate VI (Ridgway) and Empire Green, Plate XXXII (Ridgway); under surface—near Chromium Green, Plate XXXII (Ridgway). Young; upper surface—near Dark Indian Red, Plate XXVII (Ridgway); under surface—between Neutral Red, Plate XXXVIII (Ridgway) and Dark Corinthian Purple, Plate XXXVIII (Ridgway).

*Rachis (the supporting stem of the compound leaf).*—Average size. Upper side—smooth, with from few to several stipitate glands on edges. Under side—smooth, with from few to several small stipitate glands, and from none to few small prickles.

*Stipules.*—From short to medium length; medium width; with short points turning out at an angle of more than 45°.

*Disease resistance.*—Better-than-average resistance to mildew as compared to other varieties grown under comparable cultural conditions at Ontario, California.

Growth:

*Habit.*—Bushy; upright-spreading; much-branched.

*Growth.*—Free.

*Canes.*—From medium caliper to heavy.

*Main stems.*—Color—between Biscay Green, Plate XVII (Ridgway) and Light Elm Green, Plate XVII (Ridgway). Large prickles—from several to many; medium length; hooked slightly downward; with short, moderately broad base; color—near Tawny Olive, Plate XXIX (Ridgway). Small prickles—from few to several; color—near Tawny Olive, Plate XXIX (Ridgway). Hairs—none.

*Branches.*—Color—near Parrot Green, Plate VI (Ridgway). Large prickles—from few to several; medium length; hooked slightly downward; with medium-length, moderately-broad base; color—near Amber Yellow, Plate XVI (Ridgway). Small prickles—from none to few; color—near Amber Yellow, Plate XVI (Ridgway). Hairs—none.

*New shoots.*—Color—near Courge Green, Plate XVII (Ridgway), overlaid with near Sorghum Brown, Plate XXXIX (Ridgway) on side exposed to the sun. Large prickles—from few to several; medium length; hooked slightly downward; with medium length, moderately broad base; color—near Vinaceous Brown, Plate XXXIX (Ridgway). Small prickles—from none to few; color—near Vinaceous Brown, Plate XXXIX (Ridgway). Hairs—none.

I claim:

A new and distinct variety of rose plant of a class between the hybrid tea and floribunda classes, substantially as herein shown and described, characterized particularly as to novelty by the unique combination of a vigorous, upright-spreading, well-shaped, sturdily-branched plant habit, attractive, medium-sized, disease-resistant foliage, with the mature foliage being dark green in color and pleasingly contrasting with the reddish color of the new foliage, a floriferousness somewhat greater than that of the variety "Charlotte Armstrong" (Pl. Pat. No. 455), a habit of bearing the flowers on strong stems of from short to medium length, with the flowers borne sometimes singly and sometimes in small clusters, a rather short bud form ranging from ovoid to urn-shaped in shape, said buds opening into a well-formed, high-centered flower of very double petalage, a flower size ranging from medium to large, better-than-average petal substance, with attendant very long-lasting flower qualities and prolonged retention of the flower form until the petals drop, and a distinctive bright general color tonality of the flowers ranging between Currant Red and Cardinal Red, with attendant substantial absence of fading and blueing of the flower color.

No references cited.

UNITED STATES PATENT OFFICE

CERTIFICATE OF CORRECTION

Plant Patent 2,056 May 23, 1961

Herbert C. Swim

It is hereby certified that error appears in the above numbered patent requiring correction and that the said Letters Patent should read as corrected below.

In the grant, line 2, and in the heading to the printed specification, line 4, for "San Bernardino", each occurrence, read -- Ontario --.

Signed and sealed this 24th day of October 1961.

(SEAL)
Attest:

ERNEST W. SWIDER
Attesting Officer

DAVID L. LADD
Commissioner of Patents

USCOMM-DC